(12) United States Patent
Rohacek et al.

(10) Patent No.: US 8,520,215 B2
(45) Date of Patent: Aug. 27, 2013

(54) METHODS AND APPARATUS FOR INVESTIGATION OF VOLUME CHANGE DYNAMICS OF PHYSIOLOGICALLY ACTIVE SAMPLES

(75) Inventors: Karel Rohacek, Ceske Budejovice (CZ); Petr Adamek, Ceske Budejovice (CZ); Miroslav Kloz, Liberec (CZ); David Bina, Telc (CZ)

(73) Assignee: Biologicke Centrum AV CR, V.V.I Ustav Molekularni Biologie Rostlin, Ceske Budejovice (CZ)

( * ) Notice: Subject to any disclaimer, the term of this patent is extended or adjusted under 35 U.S.C. 154(b) by 253 days.

(21) Appl. No.: 12/933,734

(22) PCT Filed: Mar. 20, 2009

(86) PCT No.: PCT/CZ2009/000041
§ 371 (c)(1),
(2), (4) Date: Dec. 10, 2010

(87) PCT Pub. No.: WO2009/115061
PCT Pub. Date: Sep. 24, 2009

(65) Prior Publication Data
US 2011/0085174 A1  Apr. 14, 2011

(30) Foreign Application Priority Data
Mar. 21, 2008  (CZ) .................................... 2008-186

(51) Int. Cl.
*G01B 11/02*  (2006.01)
(52) U.S. Cl.
USPC .......................................................... 356/496
(58) Field of Classification Search
USPC ................. 356/496, 477, 478, 450, 511, 482, 356/498, 516
See application file for complete search history.

(56) References Cited

U.S. PATENT DOCUMENTS 5,257,090 A * 10/1993 Meinzer et al. ............... 356/498
6,680,780 B1   1/2004 Fee
(Continued)

FOREIGN PATENT DOCUMENTS
CZ  18611 U1  6/2008
CZ  18612 U1  6/2008
(Continued)

OTHER PUBLICATIONS

Karel Rohacek, et al; "Investigation of Non-photochemical Processes in Photosynthetic Bacteria and Higher Plants Using Interference of Coherent Radiation—A Novel Approach" Photosynthesis Research, vol. 91, No. 2-3, Feb. 2007, p. 301, XP009120972 & 14th International Congress of Photosynthesis; Glasgow, UK; Jul. 22 27, 2007; ISSN: 0166-8595 paragraph [25.6].

(Continued)

*Primary Examiner* — Gregory J Toatley
*Assistant Examiner* — Shawn Decenzo
(74) *Attorney, Agent, or Firm* — Ladas & Parry LLP (57) ABSTRACT

A transversal change of the position of a measured sample surface exposed to the influence of visible radiation for example actinic light, is measured interferometrically by a reflecting target, which is in mechanical contact with the measured sample surface, and reflects a measuring beam, generated together with a reference beam by a laser source, and the transversal change of the position of the measured sample surface is detected from the phase difference of harmonic waves in the beam of interfering radiation. The device involves, for example, a special detection connection of photodetectors, a measuring unit and a basic module with a computer, the design of reflecting targets for liquid and solid samples, an optomechanical dimension transmitter and a holder of solid samples.

8 Claims, 7 Drawing Sheets

(56) References Cited

U.S. PATENT DOCUMENTS

| | | | |
|---|---|---|---|
| 7,214,932 B2 * | 5/2007 | Brunfeld et al. | 250/234 |
| 7,224,463 B1 * | 5/2007 | Zumberge et al. | 356/450 |
| 7,230,717 B2 * | 6/2007 | Brock et al. | 356/495 |
| 2006/0114466 A1 * | 6/2006 | Bewersdorf et al. | 356/450 |

FOREIGN PATENT DOCUMENTS

| | | |
|---|---|---|
| CZ | 18613 U1 | 6/2008 |
| DE | 3303510 A1 | 7/1983 |
| DE | 4427438 A1 | 2/1996 |
| WO | 01/27557 A1 | 4/2001 |
| WO | 2005/001445 A2 | 1/2005 |
| WO | 2006/079013 A1 | 7/2006 |
| WO | 2007/014622 A1 | 2/2007 |

OTHER PUBLICATIONS

J. Květoň, et al; "Pavel Siffel (1954-2003) or Life full of chlorophyll", Photosynthetica; International Journal for Photosynthesis Research, Kluwer Academc Publishers, DO, vol. 43, No. 3, Sep. 1, 2005, pp. 323-328, XP019223771, ISSN: 1573-9058; p. 326, right-hand column, paragraph 1.

International Search Report: PCT/CZ2009/000041.

\* cited by examiner

METHODS AND APPARATUS FOR INVESTIGATION OF VOLUME CHANGE DYNAMICS OF PHYSIOLOGICALLY ACTIVE SAMPLES

CROSS REFERENCE TO RELATED APPLICATION

This application is a national stage application claiming priority from International Application No. PCT/CZ2009/000041 filed Mar. 20, 2009, and Czech Application No. PV 2008-186 filed Mar. 21, 2008, each of which is incorporated herein by reference in their entirety.

FIELD OF THE DISCLOSURE

The present disclosure deals with methods and apparatus for investigation of volume change dynamics of physiologically, particularly photosynthetically active samples, like for example higher or lower plants, algae, photosynthetic bacteria or parts of these organisms. The investigation is aimed at qualitative and quantitative determination of volume change dynamics of samples, particularly in dependence on their photosynthetic activity, while the investigation may also be performed on plants in vivo. This disclosure was supported by GA AV ČR, grant No. IAA600960716.

BACKGROUND OF RELATED ART

Research of photosynthetic activity and physiological condition of plants is most frequently based on time dependent changes of chlorophyll fluorescence. Chlorophyll, as the key photoactive pigment is present in all photosynthetic organisms and is a photoactive chromophore of all reaction centres modifying radiant energy to biochemically usable form. Most of the absorbed energy is used by the photochemical system for transfer of electrons and protons from water to the products and processes necessary for $CO_2$ fixation to sucrose molecular structure. The energy of photosynthetically active radiation (wavelength of 400-700 nm) is absorbed by antena pigments (chlorophylls and carotenoids) organized in light harvesting complexes of photosystem I and photosystem II, then it is transferred in the form of excitons to reaction centres of both the photosystems, where it is used in cascade of primary photochemical and non-photochemical processes for photosynthetic fixation of $CO_2$.

Apart from photochemical reactions there are also processes of non-photochemical nature consuming excitation energy, which leads to thermal dissipation and chlorophyll fluorescence. In healthy plants about 80% of absorbed energy is consumed by photochemical reactions, only 3-5% represent chlorophyll fluorescence and the rest (15-17%) is transformed to heat. Increase of efficiency of one component, in which absorbed energy is transformed, leads to reduction in efficiency of at least one of the remaining components in accordance with the energy conservation law.

The principle of one of the common methods of investigation of photosynthesis or more precisely measurement of its efficiency is based on the premise that increase of excitation energy consumption by photochemical reactions leads to reduction of intensity of chlorophyll fluorescence, which is measured.

This measurement method belongs to a group of so called fluorimetric methods based on pulse amplitude modulation of a signal of the induced chlorophyll fluorescence. Fluorimetry enables us to determine and quantify the contribution of photochemical and non-photochemical processes to overall reduction of chlorophyll fluorescence obtained by assessment of records of so called chlorophyll fluorescence induction kinetics. Recently, photosynthetic activities of plants in photosynthesis research are mainly derived from these curves, measured under different external and internal conditions by means of various types of fluorimeters.

The published patent application DE 4427438 describes a method of research of plant photosynthetic system, where plants undergo phases of darkness and light, and after a dark phase they are illuminated with very short light pulses generated by a laser source with perpendicular course and induced fluorescent radiation is recorded. This is a non-destructive method, but it has a disadvantage that it studies the activity of photosystems I and II in plants and does not enable studying volume dynamics of plant tissues during photosynthesis.

Disadvantage of fluorimetric methods is generally based on the fact that they are not capable to measure directly the transformation of excitation energy to heat. Measurement of thermal signal of photosynthetically active samples thus has to be performed together with fluorescence to enable full investigation of the way how plants utilize the energy absorbed during photosynthesis.

A photoacoustic method is known for measurements of heat development and processes related to the exchange of gases in chloroplasts and in plant tissue. This method is based on the photoacoustic effect, i.e. a time recording of pressure modulation in samples, which includes acoustic waves induced by radiationless deexcitation of excited states of pigment molecules, development of gas ($O_2$), fixation of gas ($CO_2$), sample surface deformations etc., as a consequence of absorption of frequency modulated light. Acoustic waves in photosynthetically active samples are a result of thermal expansion in organic materials and ambient gases, photosynthetic oxygen development and $CO_2$ uptake. Light absorption in photosynthetically active samples leads to both changes of dynamic pressure inside plant tissue cells, and volume changes of a sample as a whole.

Disadvantages of the photoacoustic method, also called photoacoustic spectroscopy, are mainly based on the fact that samples have to be measured in enclosed measurement cells, which is complicated, particularly with plants with regard to their size and positioning in a cell. This method is particularly advantageous for research of chloroplast suspensions, segments of leaves and tissues. The disadvantage is that a measured sample is separated from the mother plant, thus the measurement in so called in vivo status is impossible. The acquisition cost of the photoacoustic spectroscopy device is very high, as well.

Volume or more precisely dimensional changes may be generally measured for example by interferometric and holographic methods. The principle of exact interference measurement of distances is based on superposition of two coherent light waves (i.e. waves with a constant phase difference) which are directed at the same time to the same point. Evaluation of patterns appeared in the interference enables very exact measurement of length distances in the light wave path by means of an interferometer (e.g. so called Michelson interferometer).

The published patent application WO 01/27557 for example describes a system for interference deformation analysis in real time, which is modified for measurements in industrial environment. Phase differences of the measuring and the reference beams are recorded by means of a hologram.

Another published application WO 2005/001445 presents a method and a device for phase differential measurement of distance changes of small biological objects, particularly in the field of cell physiology and neurology, which cannot be examined in living conditions by for example X-ray. The system involves the method of optical interferometry or spectroscopy of diffuse radiation or their combination, and is intended for detection of changes in optical characteristics of the measured sample, not for measurement of the volume change dynamics in real time.

Another published application WO 2006/079013 similarly describes an interferometer with low-coherent beam for measurement of tissues of a biological sample, which directs a light beam to the first layer of the biological sample and receives the light reflected from this layer and then it directs the beam to a reflective device and receives the light reflected by the reflective device. The reflected light beams interfere and define the first phase. The second phase is defined similarly. The biological sample is evaluated upon the first phase and the second phase. The method is designed for measurement of atherosclerotic plaques in arterial system upon the index of refraction change in a sample environment.

Another known method and device for analysis of biological objects is described in a published patent application WO 2007/014 622, where the means of digital holographic micro-interferometry are used, a 3-dimensional image of biological objects, particularly cells is captured, ad it is then evaluated, except others also from the point of view of volume and dimensional changes.

Holographic techniques cannot be applied on examination of photosynthetically active samples, as exposure of a sample to laser radiation would affect the sample photosynthesis already as a consequence of the measurement radiation itself, which is undesirable for the measurement. Holograms themselves moreover do not have sufficient resolution and radiation of larger object in vivo is technically complicated.

Application of known interference measurement methods based on laser measuring beams, applied in other fields of technology, to photosynthetically active samples is also problematic. Application of intensive high energy laser beams causes a damage and destruction of samples, for example a plant leaf, as a consequence of the fact that more than 80% of the measuring beam radiation is absorbed by the sample and damages its tissue. Photosynthetically active samples (e.g. leaves) have only low reflectivity (approx. 8-12%), which is why even interferometers with low energy laser beam cannot be used, as in this case the measuring beam would not be reflected with sufficient intensity and an interferogram of sufficient quality could not be obtained.

Application of interferometers known from other field of technology is then problematic for unsuitability of their detection and measurement parameters in the field of transmission of a laser interferential pattern with variable radiation intensity on the screen to an electric signal, which may be processed and evaluated as a sample dimension change.

A known interferometric length measurement method represents counting of pulses derived from the pass of a photodetector harmonic signal through a nod (zero), while the distance change is obtained as an order multiple of wavelength or its half.

Better resolution than ½ of the wavelength of the radiation applied is required for exact measurement of physiologically, particularly photosynthetically active samples. This implies exact measurement of relative values of the amplitude of detector signals, from which the signal phase is then determined, and dimension change can be determined to a fraction of wavelength.

Complication is caused by unstable intensity of laser beam, which changes as a consequence of time and temperature instabilities of a laser generator. The noise of the detected signal, which is mainly generated by self oscillations of mechanical scanning device, is another problem. Microphone effect occurs here, building vibrations are scanned and further signals disabling exact determination of relative amplitude of photodetector signals and subsequent phase determination. The measured signal itself is burdened by noise signal, containing also coincidental effects apart from harmonic and anharmonic components.

BRIEF DESCRIPTION OF THE DRAWINGS

The examples will be explained in detail on drawings, where.

DETAILED DESCRIPTION

The below described and depicted particular examples are considered illustrative and they in no way limit the invention to the examples herein presented. Professionals in the technology sphere will find or will be able to find more or fewer equivalents to the specific examples herein described in their routine experimental work. These equivalents are also going to be included to the extent of the below patent claims.

The device for investigation of volume change dynamics of physiologically, particularly photosynthetically active samples according to the present disclosure is arranged on a non depicted optical table with a system damping ambient vibration and on a solid laboratory table. The samples include for example higher plants in vivo, bacteria, algae, chloroplast suspensions etc.

The present disclosure improves the method of interference laser measurement of distances and volume changes so as it suits to investigation of volume change dynamics of physiologically, particularly photosynthetically active samples in vivo, and to develop a device for application of this method. The disclosure is aimed at improvement of the existing research methods, and quantification and measurement of photosynthetic processes of non-photochemical nature more precisely, for example in liquid samples, vegetal samples and whole plants in the state as they live.

Within the text, the term "volume change dynamics" means continual recording of changes of sample dimensions corresponding to dimension changes expressed in tens of nanometers to micrometers, and with the time resolution expressed in milliseconds to tens of minutes.

Absorption of light radiation in higher plants (generally in all photosynthetically active organisms) results in dynamic pressure changes in leaf tissue cells as a consequence of molecular oxygen production, $CO_2$ fixation, thermal expansion, surface deformation etc. These processes cause detectable volume changes of a sample expressed at least in hundreds of nanometers. A change of sample volume thus provides the possibility to quantify thermal and other photosynthetic processes in the sample. The most accurate measurement of a transversal dimension change of the sample is thus the aim.

The aim is achieved by the method of investigation of volume change dynamics of physiologically, particularly photosynthetically active samples exposed to visible radiation. The principle of the disclosed method is based on application of measurement of transversal changes of the sample volume by means of the interference principle, while the source beam of monochromatic, highly coherent radiation of a laser source is split into two mutually perpendicular beams on the first beam splitter. The measuring beam goes through an adjustable mirror and falls on a reflective target with highly reflective surface, which is in mechanical contact with the measured sample surface, and the reference beam falls on a fixed reflective reference mirror. After the reflection and return through the first beam splitter, the measuring beam and the reference beam interfere mutually and the transversal change in a position of the measured sample surface as a result of its volume change is detected from the phase difference of harmonic waves in the interfering radiation beam. The reflecting target separates the beam of intensive laser radiation from the sample itself, so it cannot be damaged during measurement and the photosynthetic processes taking place in the sample cannot be affected. In one example, the beam of the interfering radiation is then split on the second beam splitter to two detection beams, where the first detection beam passes through the first converging lens and falls on the first photodetector, and the second detection beam perpendicular to the first detection beam passes through the second converging lens and goes to the second photodetector, while the photodetectors are mutually phase-shifted by 90° in the interferogram and the signals from the photodetectors go to a processing unit connected to a computer.

The photodetectors may be for example photodiodes, phototransistors, channeltrons or so called PIN (positive/intrinsitic/negative) detectors, i.e. detectors with so called quick PIN—diodes. Phototransistors have an advantage that they can be located next to each other in a single interferogram due to their small size.

The phase shift of the photodetectors by 90° in the recorded interferogram enables to detect the sense of the sample dimension change during subsequent evaluation of the interferogram.

In terms of protection of photodetectors against disruptive influence of ambient difuse radiation there is an advantage, if the detection beams pass through absorbers of diffuse radiation, which are cylindrical tubes whose length is an order multiple of the photodetector length, before they reach the detectors.

In another example the detection and evaluation of the interfering radiation beam is performed in the manner that the interfering radiation beam is again split to two detection beams on the second beam splitter, where the first detection beam passes through the first converging lens and falls simultaneously on the first and second photodetectors, while both the photodetectors are mutually phase-shifted by 90° in the interferogram, and the second detection beam, perpendicular to the first detection beam falls on the third photodetector, which scans the whole interference pattern, and the signals from the photodetectors go to the measuring unit connected to a computer via interface. The advantage of this method is based on suppression of noise signals of stochastic nature and in improvement of the measurement resolution. There is also an advantage if the detection beams pass through absorbers of diffuse radiation to protect the photodetectors against influence of an ambient diffuse radiation.

An advantageous procedure of processing measured signals is that the signals from the photodetectors are fed to the basic module of the measuring unit, where the signal from the third reference photodetector after processing in an amplifier sets the mean value if the radiation intensity as the reference value in the reference signal. The signals from the first and the second photodetectors are after processing in amplifiers and suppression of noise signals by low-pass type active filters transferred to symmetrical alternating signals with suppressed direct component by means of reference signal. The alternating component is separated from the first photodetector signal and then samples of alternating signals of the first photodetector and the second photodetector are taken by means of a waveform shaper and a controlling and sequential circuit emitting control signals for sampling amplifiers, for elimination of disturbing effects with big amplitudes. The voltage corresponding to the noise signal frequency is measured on the output of the controlling and sequential circuit, while the basic module is connected to a computer through A/D converters and an interface.

Detection, filtering, pre-processing and sampling of the signals and their digitalization enable subsequent quick evaluation of the sample dimension change in real time by means of a control and evaluation programme, while temperature dependence of the source and the photodetectors, as well as the noise signals of electric and mechanic origin are eliminated.

There is an advantage in measuring samples in solid state that if the reflecting target is placed on a movable optomechanical dimension transmitter provided with at least one contact tip bearing on the surface of the solid measured sample arranged in a solid sample holder in a darkening chamber, while the visible radiation from the source falls on the sample. The method is at most considerate towards the measured sample, so measurement of liquid as well as solid samples may be performed in the in vivo status.

It is also advantageous to connect a fluorimeter to the solid sample holder and the induced chlorophyll fluorescence of the sample is measured, so the time course of the fluorescence induction curve may be compared with the measured transversal dimension changes. Finally there is an advantage, if the sample surface in the solid sample holder in the darkening chamber is exposed to gaseous medium influencing the sample physiological status, so the investigation may be aimed at combination of various photosynthetically effective stimuli.

The subject matter also includes a device for investigation of volume change dynamics of physiologically, particularly photosynthetically active samples. Its principle is based on the fact that it involves an interferometer for measurement of transversal change of position of the measured sample surface, consisting of a laser source of monochromatic highly coherent radiation, of the first beam splitter splitting the source beam into a measuring beam and a reference beam, of an adjustable mirror directing the measuring beam to the sample, of a referential reflective mirror reflecting the reference beam and of at least one photodetector. A beam of the interfering radiation consisting of the reflected measuring beam and the reference beam fall on this photodetector through a converging lens. The photodetector is connected to the input of a processing unit or a measuring unit connected to a computer. The device also involves a reflecting target with highly reflective surface, which is in mechanical contact with the measured sample surface, and on which the measuring beam falls.

In another advantageous embodiment of the device, which works with a special newly designed measuring unit, a second beam splitter is arranged in the interference radiation beam path, from which the first detection beam passing through the first converging lens and falling on the first photodetector and the second photodetector comes, while the photodetectors are mutually phase-shifted by 90° in the interferogram. The second detection beam perpendicular to the fist detection beam falls on the third reference photodetector, while the outputs of the photodetectors are connected to the input of the measuring unit connected to a computer via interface. This embodiment enables evaluation and recording both, the value and the sense of the measured sample dimension change and it moreover eliminates noise signals of stochastic character during measurement and improves time and dimensional resolution of measurement.

In terms of protection of the photodetectors against disruptive influence of ambient diffuse radiation there is an advantage, if each photodetector is furnished with an absorber of diffuse radiation of cylindrical tubular shape several times longer than the photodetector.

A special measuring unit includes a basic module, which is connected to a computer through A/D converters and an interface, and in which the inputs from the first and the second photodetectors lead to an amplifier and to an active filter of low-pass type suppressing noise signals and are converted to alternating signals in differential amplifiers by subtraction of the direct component of the signal from the third photodetector and lead to sampling amplifiers. The first photodetector signal goes to a signal shaper and then to a controlling and sequential circuit, from which controlling signals for collection of samples of alternating signals in sampling amplifiers come, and which is equipped with an output of voltage corresponding to the frequency of noise signals. The output from the third referential photodetector leads to an amplifier and as a reference signal is led to a differential amplifier and is brought out as a separate output.

The application of the basic module is particularly advantageous because unlike all the devices so far known it does not count simple passes of the measurement signal through zero (nod), but the measured signals are pre-processed, digitalized and evaluated in such manner that the dimension resolution is improved under $\lambda/8$ where $\lambda$ is the wavelength of the radiation applied, and the time resolution covers the scale from milliseconds to tens of minutes. The advantage of the basic module is also based on the fact that it eliminates electronically the influence of stochastic noise signals on the measurement result and balances thermal dependence of the laser and actinic radiation source and the photodetectors.

The sample part of the design for measurement of liquid samples is advantageously solved by means of a reflecting target formed by a thin glass plate provided with a thin reflective gold layer and arranged on the surface of the measured liquid sample in a cuvette, where it is held by the surface tension forces.

In an advantageous embodiment of the sample part of the device modified for measurement of solid samples the reflecting target is arranged on a movable optomechanical dimension transmitter provided with at least one contact tip, bearing on the surface of the solid measured sample. The sample is arranged in a holder of solid samples in a darkening chamber, which is connected to a source of visible radiation falling on the measured sample. The laser beam thus does not fall directly on the surface of the measured sample and the transversal changes of the sample volume are transferred by means of the dimension transmitter to the scanned transversal change of the reflecting target position. From the point of view of design simplicity it is advantageous if the solid sample holder consists of a circular bottom flange and a circular upper flange, which are demountably attached to each other, and there is a darkening chamber for the measured sample provided between their inner sides. The upper flange is provided with a measuring aperture for the dimension transmitter contact tip and the bottom flange is provided with a closable illuminative aperture. This embodiment enables simple and quick loading and unloading of the measured sample and easy fixation of the whole holder with the sample to a stand (not depicted) on a spring-loaded optical table.

It is also advantageous if a sliding cover is pivoted on the bottom flange provided with a tubular extension for a fibre optics connected to the visible radiation source and to the fluorimeter. The sample may be lighted or dimmed by sliding the cover. The fibre optics enables both, illumination of the sample with visible light of chosen intensity or measurement of induced chlorophyll fluorescence of the sample.

It is also advantageous if annulus shaped light proof porous gaskets are attached to the inner sides of the bottom flange and the upper flange, whose inner perimeter encloses the space of the darkening chamber. A flat measured sample, e.g. a leaf, may be carefully fixed between the gaskets.

The gasket is advantageously made of black soft foam material disabling penetration of ambient light into the darkening chamber, but enabling gas exchange with the environment.

As the gasket is porous it enables ventilation of gas medium affecting the sample physiological status. For this purpose the bottom and the upper flanges are both provided with openings with pipe couplings in the gasket area for connection of gaseous medium, and with boring connecting the pipe couplings with the darkening chamber interior. The gas can thus penetrate to the measured sample surface from both sides inside the darkening chamber and leaves through the porous sealing.

In an advantageous design of the optomechanical dimension transmitter the transmitter is imbedded in horizontal position on a blade with the possibility of swing movement around a swing axis. A vertically arranged swing arm with a balance weight holding the horizontally positioned reflecting target is pivoted between the contact tip and the swing axis. The swing arm ensures the permanent horizontal position of the reflecting target even during the swing movement of the dimension transmitter. The reflecting target is advantageously attached by means of a carrier, carrying the reflective target consisting of an $Si/SiO_2$ plate with a deposited highly reflective thin layer of gold, on the top of the swing arm.

The dimension transmitter itself consists of two lightweight girders connected by at least one crossbar to the "V" shape, the contact tip is attached in the area of the "V" connection and the swing arm is attached on an axis pivoted transversally on the girders. The reflecting target is perpendicularly arranged on the top of the swing arm above the plane of the girders. For optimum balance and correct function of the dimension transmitter the distances between the contact tip and the swing arm and between the swing arm and the swing axis are in the ratio of 1:4, and this ratio is taken into account in calculation of the reflection target transversal position change to the transversal change of the dimensions of the measured sample.

The presented method of investigation of volume change dynamics of physiologically, particularly photosynthetically active samples, and the device for the method application represents a new technique of laboratory examination of photosynthesis in liquid samples, leaf segments, intact leaves and whole plants in vivo, without their destruction or damage, in real time, which represents the main advantage against the existing state of technology. Other advantages may be seen in improvement of dimension accuracy and time resolution and elimination of disturbing effects to the obtained results. The device also enables recording of time course of chlorophyll fluorescence induced in the measured sample together with the interferometric measurement, which has great importance for a quantitative determination of efficiency of the three main processes occurred during photosynthetic conversion of radiating energy—photochemistry, thermal dissipation and fluorescence. Miniaturization of the individual parts of the device will enable application of the presented method and device for examination and investigation of photosynthesis in natural (field) conditions in the near future. The device has another advantages in substantially lower price compared to photoacoustic measurement apparatuses.

Figure 9:
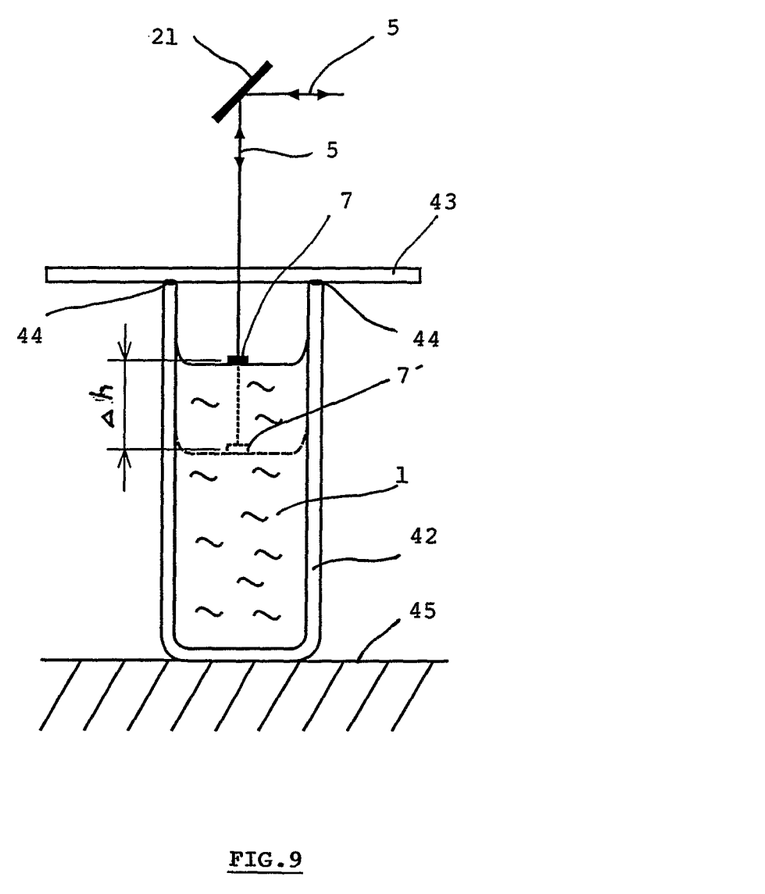
FIG. 9 shows a detail view of the sample part of the device modified for measurement of liquid samples.

The measured sample 1 may be in liquid state or in solid state. A liquid measured sample 1 depicted in FIG. 9 is in a cuvette 42 standing on a solid base 45. The cuvette 42 is arranged in a not depicted known device enabling alternation of dark phase and illumination phase with visible radiation. There is a reflection target 7 with highly reflective surface on the surface of the measured sample 1, on which a measuring beam 5 from the interferometer falls and which separates laser radiation from the sample 1.

The measured sample 1 may also be in a solid state, for example leaves or other parts of plants or even whole plants. The measured solid sample 1 is fixed in a holder 30 of solid samples in a darkening chamber 46 during examination, where it is exposed to visible radiation 23 from the source 22, and its surface is in mechanical contact with the reflective target 7 with highly reflexive surface, on which a measuring beam 5 from the interferometer falls and which separates laser radiation from the sample 1, protecting the sample against damage.

The method of investigation of volume change dynamics based on measurement of transversal change $\Delta h$ of the position of the measured sample 1 surface as a consequence of its volume change is schematically presented in FIGS. 1 through 4.

Figure 1:
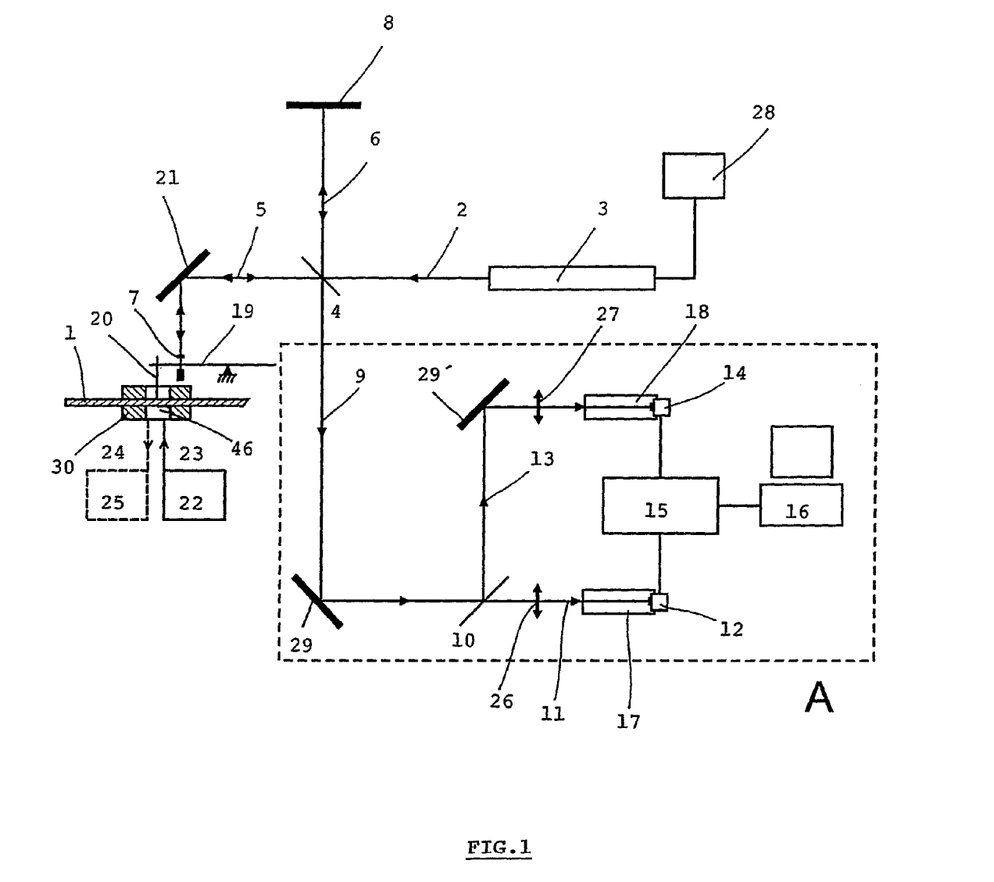
FIG. 1 shows a block diagram of the device for investigation of volume change dynamics of physiologically, particularly photosynthetically active solid samples, with two PIN-detectors, a commercial processing unit and a computer.
Figure 2:
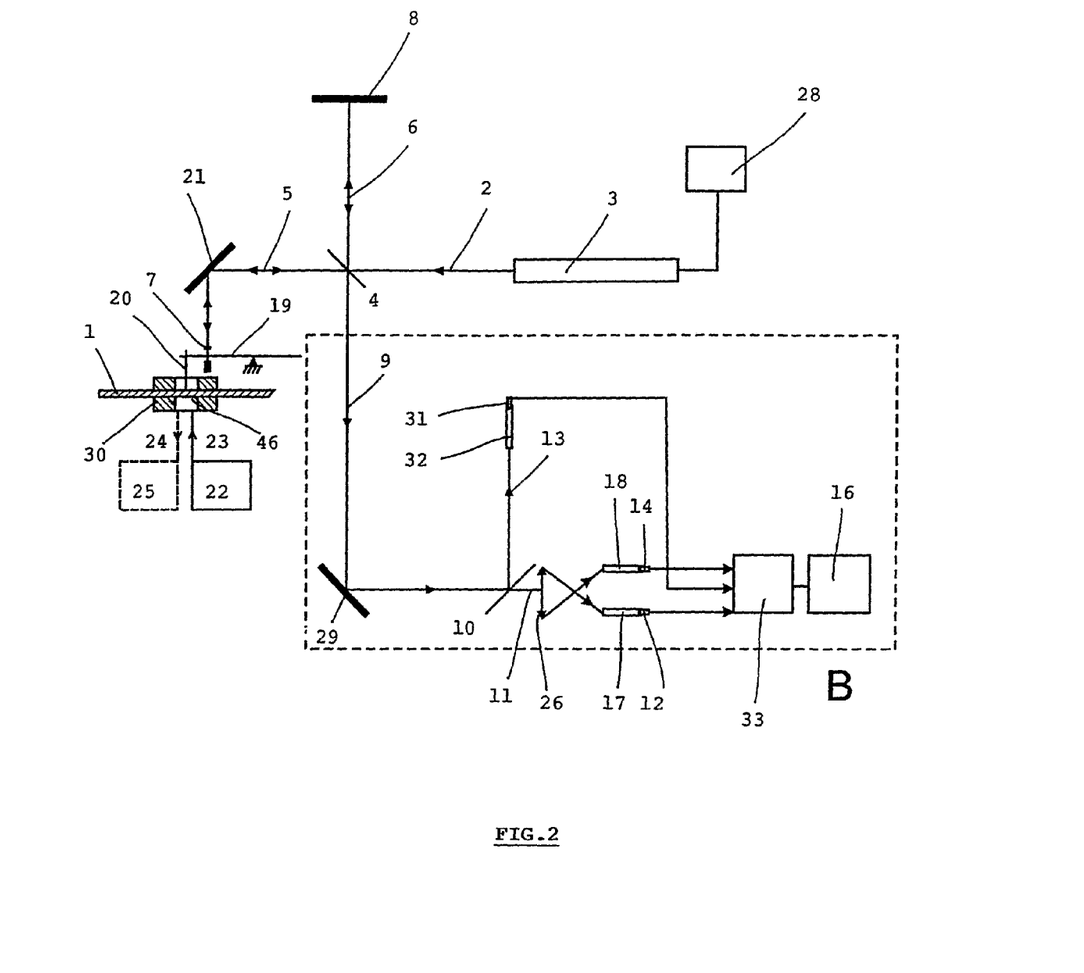
FIG. 2 shows a block diagram of the same device with three photodetectors and a special measuring module connected to a computer.
Figure 3:
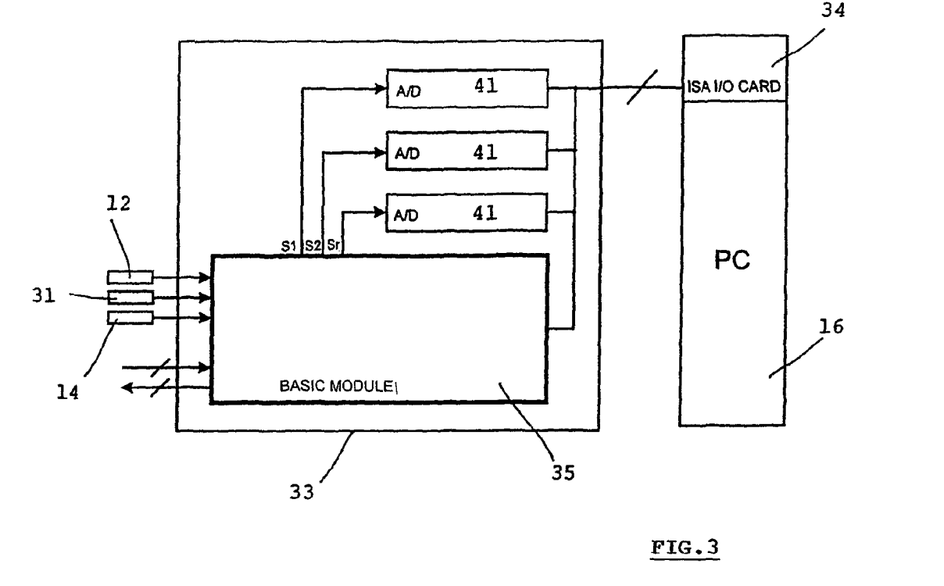
FIG. 3 shows a block diagram of the processing unit connection.

A laser source 3 of coherent radiation with a power supply unit 28 based on HeNe laser emits a source beam 2 of coherent monochromatic radiation. The source 3 continuous power is max. 15 mW, the source beam 2 diameter is smaller than 2 mm, the wavelength $\lambda$=632.8 nm. The source beam 2 is split into two mutually perpendicular beams on the first beam splitter 4. The reference beam 6 is reflected under the angle of 90°, falls on a reference reflective mirror 8 and after reflecting on it passes back through the first beam splitter 4 in straight direction. The measuring beam 5 first passes directly through the first beam splitter 4, is reflected perpendicularly down by the adjustable mirror 21, which is a standard totally reflective adjustable mirror, and falls on the reflective target 7, which is in mechanical contact with the surface of the measured sample 1. The reflective target 7 gets during movement of the measured sample 1 surface into position 7', corresponding to the transversal change $\Delta h$ of the measured sample 1 surface position, and the measuring beam 5 is reflected in real time from the positions of the reflective target 7 and 7'. After the reflection the measuring beam 5 returns back via the adjustable mirror 21 to the first beam splitter 4, on which it changes its direction by 90° and proceeds further together with the reflected reference beam 6. Both the beams 5 and 6 interfere and the transversal change $\Delta h$ of the measured sample 1 surface position as a consequence of its volume change is determined from the phase difference of the harmonic waves in the beam of interfering radiation 9.

The method and device for detection, processing and measurement of the beam of interfering radiation 9 are described in two examples corresponding to the parts of the diagrams A, B in FIGS. 1 and 2.

In the first example presented in FIG. 1 the beam of interfering radiation 9 is split on the second beam splitter 10 into two detection beams 11, 13 after reflection from the solid mirror 29. The first detection beam 11, which goes directly through the second beam splitter 10 then passes through the first converging lens 26, passes through the absorber of diffuse radiation 17 and falls on the first PIN (positive/intrinsitic/negative) detector 12. The second detection beam 13 comes out of the second beam splitter 10 perpendicularly to the first detection beam 11, is reflected under the angle of 90° by the solid mirror 29', passes through the second converging lens 27, passes through the absorber of diffuse radiation 18 and falls on the second PIN detector 14. The signals from the PIN detectors 11, 14 lead to the processing unit 15 connected to a computer 16.

The measurement and evaluation of the sample 1 is based on the known interference principle, where the path difference of the measuring beam 5 and the reference 6 is directly related to the phase difference of the harmonic waves of the interfering radiation beam 9. An interference pattern (interferogram) is the result, i.e. suitably depicted system of light and dark strips representing the places of so called constructive and destructive interference. The movement of the interference strips is changed in time in relation to the movement of the reflective target 7 and the resulting variable intensity of the interfering radiation beam 9 is scanned by means of PIN detectors 12, 14. Both the PIN detectors 12, 14 record an identical interferogram. If they are mutually phase-shifted by 90°, movement direction changes of the measured sample 1 surface in time may be identified, i.e. we can record whether the volume of the sample 1 is increasing or decreasing in this particular direction. The photosensitive surface of each PIN detector 12, 14 is 1 cm$^2$.

In the second example presented in FIG. 2 the beam of interfering radiation 9 is also split on the second beam splitter 10 into two detection beams 11, 13 after reflection from the solid mirror 29.

The first detection beam 11 passes through the first converging lens 26 and falls at the same time on the first photodetector 12 and on the second photodetector 14, both provided with absorbers of diffuse radiation 17, 18 and mutually phase shifted by 90° in the interferogram. The second detection beam 13, which comes out of the second beam splitter 10 perpendicularly to the first detection beam 11, falls on the third reference photodetector 31 also provided with an absorber of diffuse radiation 32. While the signals from the photodetectors 12, 14 give similar information for evaluation as in the first example, the third reference photodetector 31 scans the whole interference pattern and thus gives the mean value of the radiation intensity, which serves as a reference level. This method eliminates accidental changes of amplitude caused by the applied laser source 3 and also provides sufficient compensation of thermal dependence of the photodetectors 12, 14, 31.

The photodetectors 12, 14, 31 may be for example photodiodes as depicted in the diagram in FIG. 2, or phototransistors or different photosensitive elements.

If phototransistors are applied the active photosensitive surface of each is about 3 mm², thanks to the miniaturization, so they may be used in one interferogram next to one another.

Figure 4:
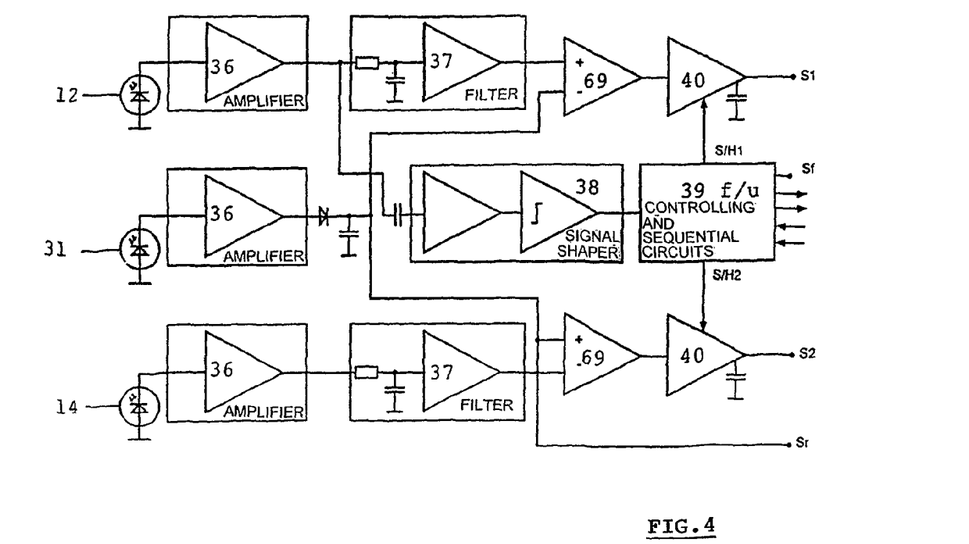
FIG. 4 shows a block diagram of the processing unit basic module.

Signals from the photodetectors 12, 14, 31 lead to a special measuring unit 33, based on the basic module 35, containing amplifiers 36, active filters 37, of low-pass type, a signal shaper 38, a controlling and sequential circuit 39, sampling amplifiers 40, signal switches, bus drivers, switching circuits, a frequency/voltage converter etc.

Signals from the photodetectors 12, 14, 31 lead to the basic module 35 in the measuring unit 33, where the third reference photodetector 31 after being processed in the amplifier 36 gives the mean value of the radiation intensity as the reference level in the reference signal (Sr), and the signals from the first photodetector 12 and the second photodetector 14 are, after processing in amplifiers 36 and after suppressing of the noise signals by the low-pass type active filters 37 are transferred to symmetric alternating signals S1, S2 with suppressed direct component by the reference signal (Sr). The alternating component of the second photodetector 12 signal is then separated by means of the signal shaper 38 and samples of alternating signals S1 and S2 from the first photodetector 12 and from the second photodetector 14 are taken by means of the controlling and sequential circuit 39, which transmits the controlling signals S/H1 and S/H2 for the sampling amplifiers 40 to eliminate disturbing effects with high amplitudes. Voltage Sf corresponding with the frequency of noise signals is measured on the output from the controlling and sequential circuit 39. The basic module 35 is connected to the computer 16 through three A/D converters 41 and the interface 34.

The active low-pass type filters 37, which suppress noise signals, while the direct component remains preserved, are used for suppression of noise signals of mechanical as well as electrical origin (undesirable higher frequencies and higher harmonic components of accidental signals). The basic frequency of noise signals may be monitored by measurement of voltage at the output Sf from the frequency/voltage convertor in the controlling and sequential circuit 39. The signal from photodetectors 12, 14 of the interferogram is transferred to symmetrical alternating signal S1, S2 with suppressed direct component by means of the reference level Sr after filtration in filters 37. Upon the signals from the photodetectors 12, 14 mutually phase-shifted by 90°, it is possible to determine the sense of the transversal change $\Delta h$ of the measured sample 1 surface position and also its phase, in other words the size of the change $\Delta h$ of the sample 1 dimension, retrospectively from the signal amplitude.

The basic module 35 is provided with the possibility of synchronous detection of the values of the signals S1, S2 from the photodetectors 12, 14 of the interferogram, for elimination of accidental and some periodical disturbing effects of high amplitudes. The alternating component is separated from the signal S1 of the photodetector 12. The signal alternating component phase is then used for synchronous sampling of signals S1, S2 by means of the controlling and sequential circuit 39 cooperating with the computer 16.

Pre-processing of the measurement outputs in the basic module 35, i.e. in the measuring unit 33, enables consequential quick evaluation of the volume change dynamics of the measured sample 1 with controlling and evaluation software.

The programme algorithm enables evaluation of the recorded interferogram, i.e. recalculation of the phase difference of the measuring beam 5 and the reference beam 6 to path difference, which is a linear scale of the transversal change $\Delta h$ of the measured sample 1 surface position, on-line in real time.

The next example presented in FIGS. 5 through 8 solves the sample part of the device for measurement on plants in vivo, on detached plant leaves or on other parts of plants.

Figure 5:
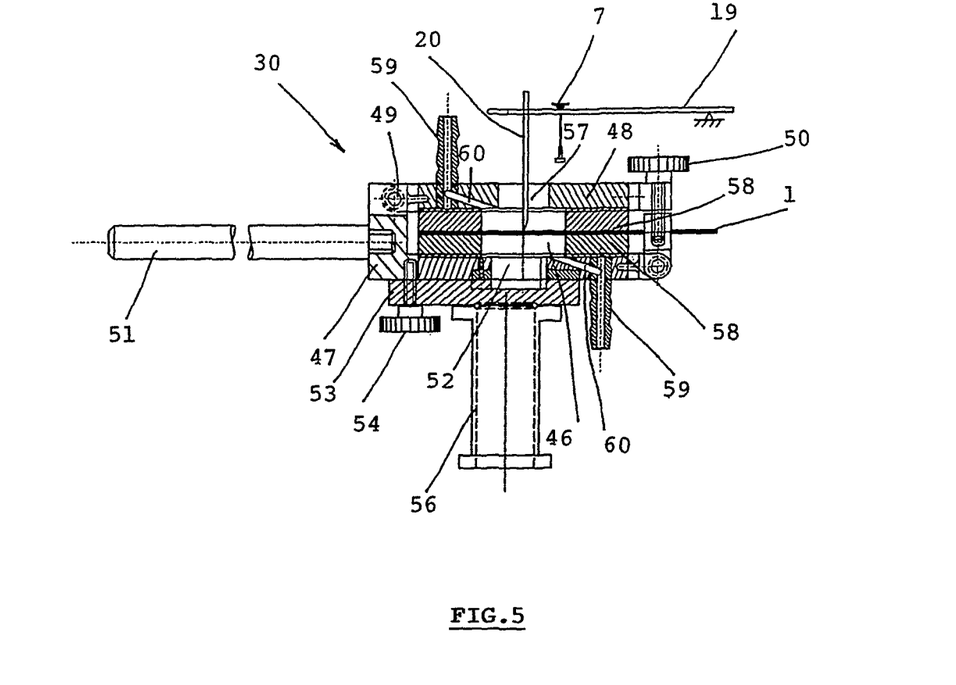
FIG. 5 shows a vertical cross section of the holder of solid samples.
Figure 6:
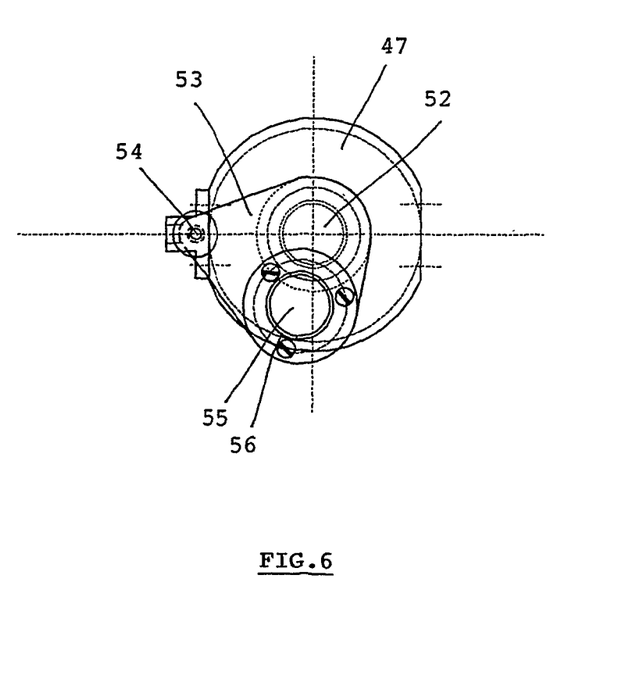
FIG. 6 shows a bottom view of the bottom flange of the solid sample holder.

The multifunctional holder 30 of solid samples 1 presented in FIGS. 5 and 6 enables attachment of solid samples 1, both, detached leaves and parts of plants (e.g. intact leaves, stems) in vivo in the darkening chamber 46, and handling the samples 1 during their examination. The holder 30 is made of aluminium alloy and consists of a circular bottom flange 47 and a circular upper flange 48, which are mutually connected on one side by means of a pivot 49 and on the other side by a locking screw 50. The measured sample 1 is placed between the flanges 47 and 48 after opening the upper flange 48, the upper flange 48 is closed and locked with the locking screw 50. A supporting arm 51, which may be clamped into a clamping fixture, is attached to the bottom flange 47. There is a darkening chamber 46 created inside the holder 30, and the bottom flange 47 is provided in the darkening chamber 46 area with an illuminative aperture 52, which may be covered with a sliding cover 53 attached in pivoted manner to the bottom side of the bottom flange 47 with an adjusting screw 54. The sliding cover 53 is integral in a part of its extent so in one angular position it covers the illuminative aperture 52, and in another part it is provided with an aperture 55 with a tubular extension 56 corresponding in another angular position of the sliding cover 53 to the position of the illuminative aperture 52. The tubular extension 56 serves for insertion of a not depicted cylindrical end of a multi-armed fiber optics, in which some arms lead visible radiation 23 (e.g. actinic light) from the source 22 to the surface of the measured sample 1 and one arm leads induced fluorescence 24, which may be measured with a fluorimeter 25 as depicted in FIGS. 1 and 2. The holder 30 thus enables simultaneous or separated performance of fluorescent and interferential measurements of solid samples 1.

The upper flange 48 is provided with a measuring aperture 57, through which a contact tip 20 of the optomechanical dimension transmitter 19 goes and slightly bears on the surface of the measured sample 1 and transmits the transversal change $\Delta h$ of the position of the measured sample 1 surface as a consequence of its volume change to the reflective target 7, where the position change is dynamically followed by a measuring beam 5 and consequently evaluated upon interference with the reference beam 6 (see FIG. 1 and FIG. 2).

The inner sides of the bottom flange 47 and the upper flange 48 are provided with annulus shaped gaskets 58, made of black soft foam material based on polyurethane, which is impermeable for light but permeable for air. The gaskets 58 enable both, careful fixation of the sample 1 in a defined position in the holder 30, and darkening a part of the sample 1 in the darkening chamber 46, and finally they also enable ventilation with gas mixture, particularly with air enriched or depleted by $CO_2$ and $O_2$ inside the darkening chamber 46, and their effect on the photosynthetic apparatus of the measured sample 1. For this there are pipe couplings 59 on the bottom flange 47 and the upper flange 48 through which the gas may be pumped through the boring 60 inside the darkening chamber 46. The measured sample 1 can thus be affected with temperature, with a visible radiation 23 from the source 22 and with exposure to gases through pipe couplings 59 and the gasket 58.

Figures 7, 8:
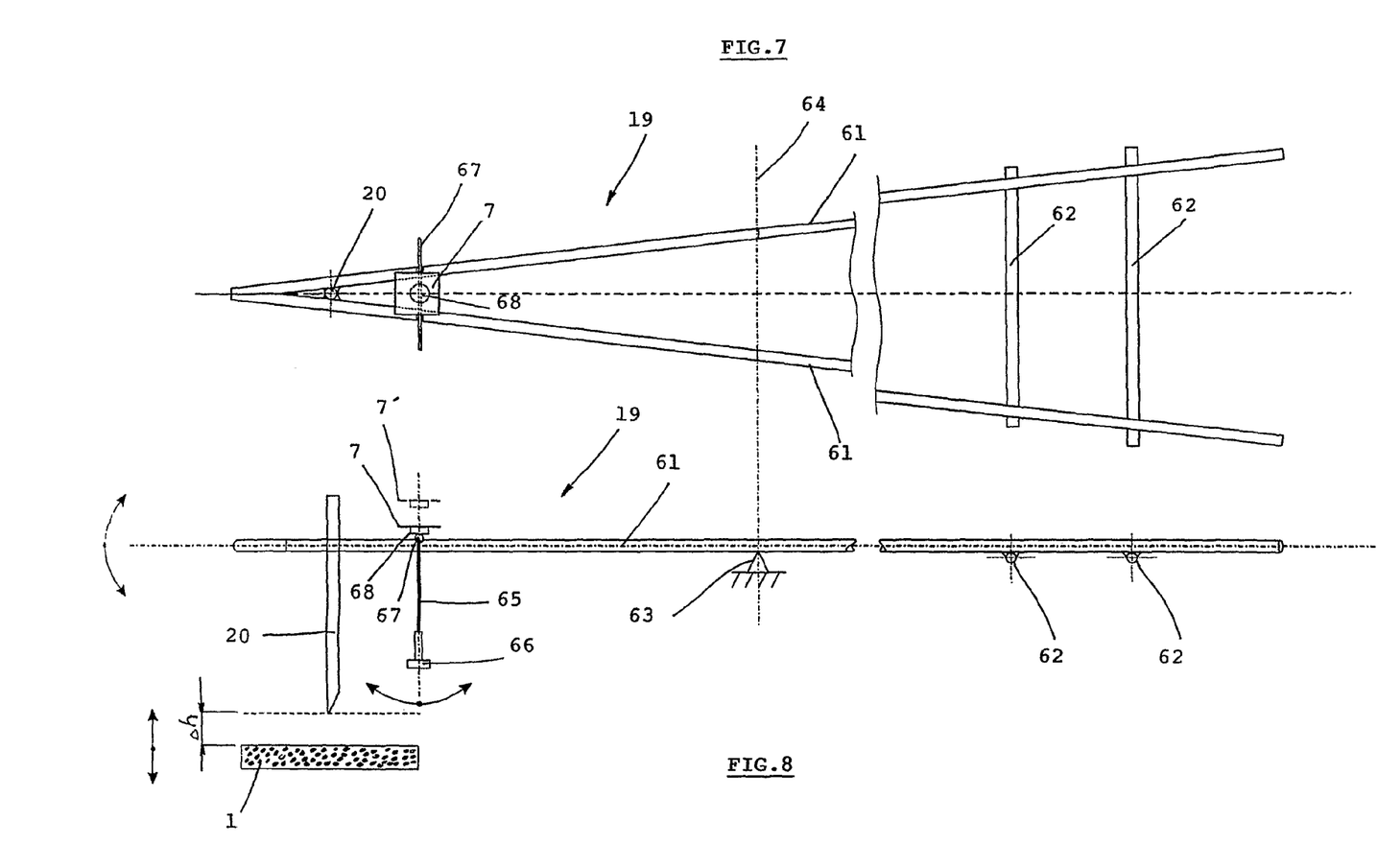
FIG. 7 shows a top view of the optomechanical dimension transmitter.
FIG. 8 shows a side view of the optomechanical dimension transmitter.

The optomechanical dimension transmitter 19 serves for transmitting transversal volume changes of the measured sample 1 fixed in the holder 30 during examination of higher plants, both, the whole plants in vivo and their separated parts.

The transmitter 19 is made of two girders 61 of lightweight material, e.g. of wood, plastic etc., mutually connected into "V" shape and reinforced with crossbars 62. The contact tip 20 with a stylus bearing on the measured sample 1 surface is attached in the place of the "V" connection perpendicularly to the girders 61. The transmitter 19 is imbedded in horizontal position on a fixed blade 63 with the possibility of swing movement around a swing axis 64, while the swing movement is realized into very small angular limits, in dependence on the movement of the measured sample 1, e.g. a leaf surface. Between the contact tip 20 and the swing axis 64 a swing arm 65 is vertically arranged, with a balance weight 66, which is pivoted on an axis 67 crossing the girders 61 and imbedded in small recesses in the girders 61. The swing arm 65, the balance weight 66 and the axis 67 are metallic. A reflective target 7 consisting of a highly reflective layer of gold deposited on a $Si/SiO_2$ plate is attached on top of the swing arm 65 above the girders 61 on a carrier 68. The reflective target 7 is attached on the swing arm 65 to remain permanently in the horizontal position or in the position 7' corresponding to the transverse change when the transmitter 19 moves as a consequence of transversal change of the sample 1 surface position. The balance weight 66 at the end of the swing arm 65 holds it in this horizontal position.

The position 7' change of the reflective target 7 is dynamically followed by the measuring beam 5 and consequently evaluated upon interference with the reference beam 6 (see FIG. 1 and FIG. 2).

Location of the reflecting target 7 on the dimension transmitter 19 between the contact tip 20 and the swing axis 64 is in the ratio of 1:4, and this proportion has to be applied on the recorded transversal change of position 7' for recalculation of the size of the transversal volume change of the measured sample 1. The reflective target 7 separates the strong laser measuring beam 5 from the photosynthetically active leaf tissues of the sample 1, to prevent them from damage and from influence of the photosynthetic processes inside the sample 1.

Another example in FIG. 9 shows the sample part of the device modified for measured liquid samples 1 in a cuvette 42 with the reflective target 7 held on the surface of the measured sample 1 by surface tension forces mainly thanks to its small dimensions and low weight. The reflective sample 7 for liquid samples 1 is made as follows: a thin glass plate of dimensions 18×18×0.05 mm is cut into square targets 7 of size between 3-4 mm and weight 5-6 mg. The surface of the targets 7 is cleaned with 30% solution of chrome-sulphuric acid or hydrogen peroxide, then rinsed with distilled water in an ultrasound washer for 10-15 minutes and dried. A highly reflective layer of gold of total thickness of several hundred manometers is deposited onto the surface of the targets 7 applying the vacuum coating method.

Measurement of liquid samples 1 is performed either in an open cuvette 42, when the water phase of the sample 1 vaporization has to be taken into account, or the cuvette 42 is covered with covering glass 43 fixed with sealing compound 44.

Figure 10:
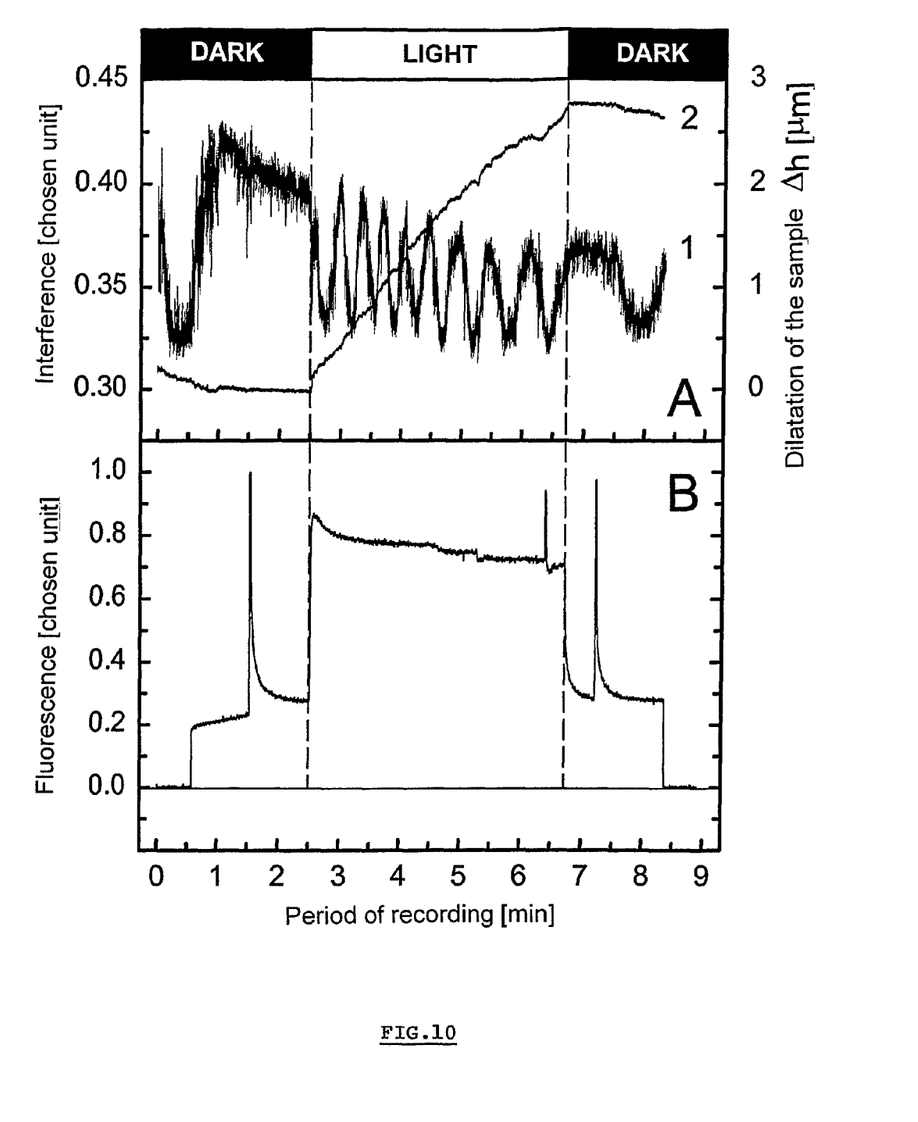
FIG. 10 shows an example of outputs of the device for investigation of volume change dynamics according to the disclosure.

FIG. 10 shows an example of simultaneous measurement with an interferometer (part A) and fluorimeter (part B) on a photosynthetically active sample 1, in this case on isolated pea chloroplasts in a closed cuvette 42. Transversal dilatation changes $\Delta h$ of the measured sample 1 (curve 2, part A), which may be compared with the course of a slow fluorescence induction curve of chlorophyll a (part B) were calculated from the interferogram (curve 1, part A).

The method and equipment for investigation of volume change dynamics of physiologically, particularly photosynthetically active samples and the device for application of the method may be used in interferential analysis of volume changes of samples, like for example higher or lower plants, algae, photosynthetic bacteria or parts of these organisms, or other physiologically active samples even in the in vivo conditions and particularly in real time.

OVERVIEW OF THE REFERENCES USED IN THE DRAWINGS 1 measured sample
$\Delta h$ transversal change of the sample surface position
2 source beam of a monochromatic coherent radiation
3 laser source of radiation
4 first beam splitter
5 measuring beam
6 reference beam
7 reflecting target
7' position of the reflecting target after the transversal change
8 reference reflecting mirror
9 beam of interfering radiation
10 second beam splitter
11 first detection beam
12 first photodetector
13 second detection beam
14 second photodetector
15 processing unit
16 computer, PC
17 light absorber of the first detector
18 light absorber of the second detector
19 optomechanical dimension transmitter
20 contact tip of the o.-m. dimension transmitter
21 adjustable mirror
22 source of VIS radiation
23 visible radiation
24 induced fluorescence
25 fluorimeter
26 first converging lens
27 second converging lens
28 power supply unit of the laser source
29 fixed mirror
29' fixed mirror
30 holder of solid samples
31 third reference detector
32 light absorber of the third reference PIN-detector
33 measuring unit
34 interface
35 basic module of the measuring unit
36 amplifier
37 active filter
38 signal shaper
39 controlling and sequential circuits
40 sampling amplifier
41 A/D (analogue-to-digital) converter
42 cuvette
43 cover glass
44 sealing compound
45 solid pad
46 darkening chamber
47 bottom flange
48 upper flange
49 pivot
50 locking screw
51 supporting arm
52 illuminative opening/aperture 53 sliding cover
54 adjusting screw
55 aperture
56 tubular extension
57 measuring aperture
58 seal
59 pipe coupling
60 boring
61 girder
62 crossbar
63 blade
64 swing axis
65 swing arm
66 balance weight
67 axis
68 carrier
69 differential amplifier

The invention claimed is:

1. A method of investigation of volume change dynamics of physiologically active samples exposed to a source of visible radiation comprising:

splitting a source beam of monochromatic highly coherent radiation produced by a laser source in two mutually perpendicular beams on a first beam splitter, of which a measuring beam falls via an adjustable mirror on a reflective target with highly reflective surface, which is in mechanical contact with a surface of a measured sample, and a reference beam falls on a fixed reference reflective mirror, after reflection and backward pass through the first beam splitter the measuring beam and the reference beam interfere, determining a transversal change of the measured sample surface position as a consequence of a volume change of the measured sample from a phase difference of harmonic waves in an interfering radiation beam, splitting the interfering radiation beam into two detection beams on a second beam splitter, where the first detection beam passes through a first converging lens and falls simultaneously on a first photodetector and on a second photodetector, while the first and second photodetectors are mutually phase-shifted by 90" in a resultant interferogram, and the second detection beam, perpendicular to the first detection beam falls on a third photodetector, which scans a whole interference pattern, while the first and second detection beams before respectfully falling on the first and second photodetectors pass through absorbers of diffuse radiation, formed by cylindrical tubes whose length is an order multiple of a length of the first and second photodetectors, wherein signals from the first and second photodetectors lead to a processing unit, connected to a computer via an interface and signals from the first and second photodetectors lead to a basic module in a measuring unit, where a third reference photodetector after being processed in an amplifier gives a mean value of radiation intensity as a reference level in a reference signal, and signals from the first photodetector and the second photodetector, after processing in amplifiers and after suppressing of noise signals by low-pass type active filters, are transferred to symmetric alternating signals with suppressed direct component by the reference signal, separating the alternating component of the second photodetector signal by a signal shaper, taking samples of alternating signals from the first photodetector and from the second photodetector by a controlling and sequential circuit, transmitting controlling signals for sampling amplifiers to eliminate disturbing effects, and measuring with high amplitudes and voltage corresponding to frequencies of noise signals on the output from the controlling and sequential circuit, while the basic module is connected to the computer through three A/D converters and an interface.

2. The method according to claim 1, wherein the reflective target is located on a movable optomechanical dimension transmitter, provided with at least one contact tip bearing on a surface of a solid sample arranged in a solid sample holder in a darkening chamber, while visible radiation from a source falls on the solid sample and a fluorimeter is attached to the solid sample holder and further comprising:

measuring chlorophyll fluorescence of the solid sample while the surface of the solid sample in the solid sample holder in the darkening chamber is exposed to gaseous medium influencing a physiological status of the solid sample.

3. A device for investigation of volume change dynamics of physiologically active samples equipped with a source of visible radiation for initiation of volume changes of a measured sample comprising:

an interferometer for measurement of transversal change of position of the measured sample surface, comprising:
    a laser source of monochromatic highly coherent radiation,
    a first beam splitter splitting a source beam into a measuring beam and a reference beam,
    an adjustable mirror directing the measuring beam to the sample,
    a referential reflective mirror reflecting the reference beam, and
    a first photodetector adapted to receive an interfering radiation beam via a converging lens in which the interfering radiation beam comprises the reflected measuring beam and the reference beam and the first photodetector is connected to the input of at least one processing unit or a measuring unit connected to a computer,
    a reflecting target with highly reflective surface on which the measuring beam falls, the target being in mechanical contact with the measured sample surface, and
    a second beam splitter arranged to split the interference radiation beam into first and second detection beams,
    a first converging lens arranged in the path of the first detection beam, between the second beam splitter and the first photodetector, the first photodetector being arranged to receive an in phase area of the first detection beam and
    a second photodetector arranged in a parallel manner to the first photodetector, the second photodetector being arranged to receive a 90" phase-shifted area of the first detection beam
    a reference photodetector arranged to receive the second detection beam perpendicular to the first detection beam,
the first and second photodetectors and the reference photodetector connected to the measuring unit, and
a computer interfaced to the measuring unit, and
the first photodetector, the second photodetector and the reference photodetector are provided with diffuse radiation absorbers.

4. The device according to claim 3, further comprising:
a basic module being comprised in the measuring unit, an A/D converter interfacing together the basic module and the computer;
the basic module comprising:
inputs from the first and second photodetectors
amplifiers coupled to the inputs of the first and second photodetectors;
low-pass filters for suppressing noise signals coupled to the amplifiers,
differential amplifiers coupled to the low pass filters,
sampling amplifiers coupled to the differential amplifiers,
an input from the reference photodetector,
an amplifier coupled to the input from the reference photodetector,
the rectified output signal of the amplifier coupled to the differential amplifiers and brought out as a separate output,
a signal shaper connected between the amplifier and low pass filter coupled to the first photodetector and
a controlling and sequential circuit coupled to the signal shaper.

5. the device according to claim 3, wherein the reflective target comprises a glass plate with a thin reflective gold layer, the target being arranged on the surface of the measured sample in a cuvette, wherein the measured sample is a liquid.

6. The device according to claim 3 comprising:
   a darkening chamber connected to a source of visible radiation falling on the measured sample, the measured sample being arranged in the darkening chamber,
   a holder in which the measured sample is arranged, the holder being arranged in the darkening chamber, wherein the measured sample is a solid,
   a movable optomechanical dimension transmitter on which the reflective target is arranged
   a contact tip connected with the optomechanical dimension transmitter.

7. The device according to claim 6, wherein the holder comprises:
   a circular bottom flange and a circular upper flange demountably attached to each other,
   the darkening chamber for the measured sample arranged between the inner sides of the circular upper flange and of the circular bottom flange,
   a measuring aperture for the optomechanical dimension transmitter contact tip arranged in the upper flange
   a closable illuminative aperture arranged in the bottom flange
   a sliding cover pivoted on the bottom flange, the sliding cover provided with a tubular extension for a fibre optics connected to the source of visible radiation and to a fluorimeter, and
   annulus shaped light proof porous gaskets attached to the inner sides of the bottom flange and of the upper flange, the inner perimeter of which encloses the space of the darkening chamber, and between which the measured sample is arranged, the gaskets being made of black soft foam material
   pipe couplings arranged in the gasket area for connection of gaseous medium, and
   borings connecting the pipe couplings with the darkening chamber interior.

8. The device according to claim 6, wherein
the optomechanical dimension transmitter is imbedded in horizontal position on a blade capable of swing movement around a swing axis and a vertically arranged swing arm with a balance weight;
the swing arm holds the horizontally positioned reflecting target on its top and being pivoted between the contact tip and the swing axis;
the reflecting target comprises an $Si/SiO_2$ plate with a deposited highly reflective thin layer of gold and is arranged on the top of the swing arm;
the dimension transmitter comprises two girders connected by at least one crossbar to form a "V" shape;
the contact tip is attached in the area of the "V" connection and
the swing arm is attached on an axis pivoted transversally on the girders and
the reflecting target is perpendicularly arranged on the top of the swing arm above the plane of the girders and the distances between the contact tip and the swing arm and between the swing arm and the swing axis are in the ratio of 1:4.

* * * * *